United States Patent
Margulies et al.

(10) Patent No.: US 12,083,155 B2
(45) Date of Patent: *Sep. 10, 2024

(54) EDIBLE OIL COMPOSITIONS TO TREAT ORAL COMPLICATIONS AND METHODS OF USING SAME

(71) Applicant: VITA ICE THERAPEUTICS LLC, Gladwyne, PA (US)

(72) Inventors: Mark Margulies, Gladwyne, PA (US); Dennis L. Zak, Doylestown, PA (US)

(73) Assignee: VITA ICE THERAPEUTICS LLC, Gladwyne, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/383,368

(22) Filed: Jul. 22, 2021

(65) Prior Publication Data
US 2023/0277615 A1    Sep. 7, 2023

Related U.S. Application Data

(63) Continuation of application No. 14/609,301, filed on Jan. 29, 2015, now Pat. No. 11,103,546.

(60) Provisional application No. 61/932,894, filed on Jan. 29, 2014.

(51) Int. Cl.
| | | |
|---|---|---|
| A61K 36/889 | (2006.01) |
| A23D 9/00 | (2006.01) |
| A61K 36/00 | (2006.01) |
| A61K 36/185 | (2006.01) |
| A61K 36/28 | (2006.01) |
| A61K 36/31 | (2006.01) |
| A61K 36/48 | (2006.01) |
| A61K 36/63 | (2006.01) |
| A61K 36/87 | (2006.01) |
| A61K 45/06 | (2006.01) |

(52) U.S. Cl.
CPC .............. *A61K 36/889* (2013.01); *A23D 9/00* (2013.01); *A61K 36/185* (2013.01); *A61K 36/28* (2013.01); *A61K 36/31* (2013.01); *A61K 36/48* (2013.01); *A61K 36/63* (2013.01); *A61K 36/87* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 10,512,856 B1 * | 12/2019 | Jackson | B01D 11/0492 |
| 11,083,765 B2 * | 8/2021 | Davis | A61K 31/05 |
| 11,103,546 B2 * | 8/2021 | Margulies | A61K 45/06 |
| 2002/0168334 A1 | 11/2002 | Jacob et al. | |
| 2003/0236217 A1 | 12/2003 | Shalwitz et al. | |
| 2005/0222250 A1 | 10/2005 | Rezvani | |
| 2008/0299050 A1 | 12/2008 | Bortz et al. | |
| 2010/0178273 A1 | 7/2010 | Rottiers | |

FOREIGN PATENT DOCUMENTS

WO     2011126537     10/2011

* cited by examiner

*Primary Examiner* — Aaron J Kosar
*Assistant Examiner* — Randall O Winston
(74) *Attorney, Agent, or Firm* — Richard J. Brown; Reed Smith LLP

(57) ABSTRACT

A composition includes at least one edible oil for treating oral complications and providing nutrition by administering such composition.

13 Claims, 2 Drawing Sheets

EDIBLE OIL COMPOSITIONS TO TREAT ORAL COMPLICATIONS AND METHODS OF USING SAME

CROSS-REFERENCE TO RELATED APPLICATION

The present application is a Continuation application of U.S. patent application Ser. No. 14/609,301, filed Jan. 29, 2015 which claims priority to U.S. Provisional Application No. 61/932,894, filed Jan. 29, 2014 and entitled "Edible Oil Compositions to Treat Oral Complications and Methods of Using Same," which is herein incorporated by reference in its entirety.

BACKGROUND

Disorders of the mouth and throat adversely affect the comfort and health of a growing number of individuals in the United States and worldwide. Such disorders result in, for example, dryness or discomfort of the mouth and throat of patients. These disorders may be at least partially attributed to symptoms from chemotherapy and radiation treatments, HIV, anemia, Sjögren's syndrome, Dysphagia, over 400 medications, and others. Relief products for dry mouth and irritation include lozenges, sprays, gels, liquids, and cotton swabs. Although these products provide varying degrees of effectiveness, they do not deliver significant or appreciable calories or nutrition in any form. It is important to note that one of the key concerns with the aforementioned patients is not only their lack of appetite, but their inability to eat caused by oral complications. Currently-available supplements in the form of, for example, drinks, powdered mixtures, meal-replacement bars, and frozen compositions attempt to provide calories/energy for malnutrition, but do not provide prolonged and/or significant relief in the mouth.

Within the use of oral relief products there is a deeper focus on functionality than on consumer pleasure. Other than lozenges, which may have various flavors and a candy-like mouth feel, relief products like gels, sprays, and cotton swabs are not necessarily desired by the consumer. People that are experiencing a lot of oral pain may be forced into using these items, but the people that can manage the pain without these products may not use them, as they are not naturally occurring food or beverage products that people regularly consume. Another concern with some of these products is their lack of dispersion. Other than liquids, which can be swished or otherwise moved around in the mouth, remedies like sprays, gels and lozenges only treat a relatively small area. Although most patients can maneuver or otherwise move lozenges around in their mouth, they do not cover a wide area because lozenges are relatively compact or small. Patients that are experiencing oral complications and struggling to consume food are usually affected in multiple areas in the mouth. Therefore, it is more difficult for such patients to pinpoint one or more specific areas with a spray or gel. Cotton swabs may be more efficient in targeting multiple areas, but they are the most uncomfortable and unnatural form of relieving oral irritation. On the contrary, liquids can be quite effective in soothing the mouth, but most of them cannot be safely swallowed or otherwise consumed due to the ingredient composition. Thus, it is more difficult to reach deeper areas in the throat with known liquids.

The supplements that are intended to deliver calories, energy, nutrition, and other related substances are typically found in the form of drinks, shakes, powdered mixtures, meal replacement bars, and some frozen compositions. These substances may include essential additives like vitamins, minerals, fatty acids, amino acids. The supplement market is important since 20% to 40% of cancer patients die from causes related to malnutrition and 80% of cancer patients develop some form of clinical malnutrition (source: National Cancer Institute). However, depending upon the severity of the oral and throat irritation, some or all of these products may be hard to swallow. Bars are rarely recommended to patients with oral complications because of their rough and dry textures. Although shakes and frozen oriented supplements may be easier to consume, they still require frequent swallowing, which can be harsh on the irritated throat.

Most patients in the categories above that are experiencing oral complications either have a lack of appetite or enough pain in the mouth that in some way limits their caloric intake. The gels, sprays, and liquids described above do not provide any prolonged moisturizing sensation in the mouth. Therefore, patients with sore mouths or the inability to see food as appetizing are reluctant to use these supplements even when they are experiencing malnutrition or low levels of energy. In addition, most of the shake supplements require a relatively large serving size of at least 8 ounces, which forces the patient to swallow frequently to consume most of the product. Ideally, it would be best if the patient only had to swallow a few times to consume the recommended amount of calories.

SUMMARY

The composition of the present disclosure provides soothing relief for throat irritation and oral mucositis, for example, caused by infection, surgery, medication and the side effects of chemotherapy and radiation treatment. The composition simultaneously provides patients with oral relief and nutrition. The composition bridges the gap between oral relief products and dietary supplements by providing a good tasting, soothing product that offers relief from sore throats and mouths, while delivering substantial caloric value in a relatively small service size (e.g., 1.2 ounces). In one embodiment, the composition may coat a patient's mouth and/or throat, as well as moisturize the mouth and/or throat, for less painful swallowing. The composition may alleviate or eliminate dry mouth, sore throat, oral thrush, oral mucositis and/or malnutrition due to limited food intake.

BRIEF DESCRIPTION OF THE DRAWINGS

The present disclosure may be better understood by reference to the description above in conjunction with the accompanying drawings. For the purpose of illustrating the present disclosure, there are shown in the drawings embodiments which are presently preferred. It should be understood, however, that the present disclosure is not limited to the precise arrangements and instrumentalities shown. In the drawings.

DESCRIPTION

Figure 1:
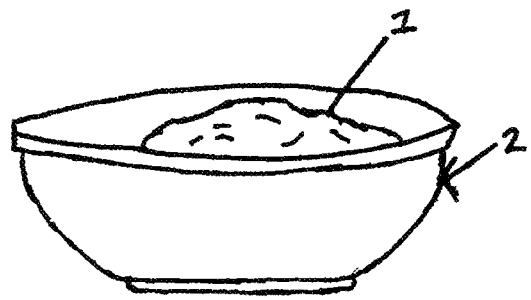
FIG. 1 is a perspective view of an exemplary form of cup packaging containing an exemplary embodiment of a frozen form according to the present disclosure.

Certain terminology is used in the following description for convenience only and is not limiting. Unless specifically set forth herein, the terms "a," "an" and "the" are not limited to one element but instead should be read as meaning "at least one." The terminology includes the words noted above, derivatives thereof and words of similar import.

The present disclosure is generally directed to a composition including at least one edible oil that at least partially moisturizes the mouth, thereby treating or at least partially alleviating oral complications, and provides an appreciable amount of calories for patients. The edible oils may be saturated or unsaturated fats. In at least one embodiment, the composition of the present disclosure is designed to treat or alleviate oral mucositis. The present disclosure is also generally directed to production, packaging, administering and/or consuming the composition. While the composition of the present disclosure may be particularly beneficial to human patients, pets struggling with oral and/or throat discomfort may benefit from the composition.

A purpose of the edible oil composition is to treat oral complications and/or irritations by at least partially moisturizing oral tissues, while simultaneously or concurrently providing calories for patients in need. Specific audiences of patients that are experiencing irritation in the mouth typically struggle to consume food, but are eager to treat their pain. These patients, who may also be experiencing lack of appetite, are generally not enticed to eat just for the sake of nutrients and energy. Thus, functional foods and previously available supplements are undesirable.

Edible oils are among the most abundant cooking ingredients in the world. They are extracted from plants (e.g., soybean, canola, and chili), seeds (e.g., sesame and sunflower), nuts (e.g., walnut and macadamia), and fruits (e.g., palm, olive, and coconut). Depending on oil type, they are used in baking and frying food, and for non-cooking products, such as salad dressing, margarine spreads, and dips. In addition, edible oils are used to produce non-food products such as cosmetics and as a feedstock for making biodiesel fuel. In the cosmetic industry, however, oils are only used for skin application and not intended for oral consumption.

In the food industry, it is known that dips, spreads, dressings, and cooking oils contain a large percentage of oils. However, these products are not consumed directly or alone. Dressings, dips, and spreads are always used in combination with other products, such as lettuce, crackers, or bread. Cooking oils are used specifically for cooking, and would also be undesirable for direct consumption. There are high percentages (25%-100%) of edible oils used in high calorie supplements and tube feeding applications; however, these are not intended for direct consumption. Tube Feeding of course is injected into the body and high calorie products such as BENECALORIE™ is mixed with other foods. These items would not be at all desirable to eat alone. In contrast, in at least some embodiments of the present disclosure, the edible oil composition is intended to be consumed directly and not in combination with other products.

One aspect of the present disclosure is directed to a method of treating an oral complication by orally administering or consuming a composition having at least one edible oil. The composition may include as many as two, three, four, five or more edible oils. Examples of suitable edible oils for the embodiments of the present disclosure include, but are not limited to, sunflower oil (including high oleic sunflower oil), safflower oil (including high oleic safflower oil), olive oil, coconut oil, palm oil, peanut oil, soybean oil, linseed oil, rapeseed oil, flaxseed oil, hempseed oil, cocoa butter, walnut oil, corn oil, grape seed oil, sesame oil, groundnut oil, wheat germ oil, cottonseed oil, fish oil, watermelon seed oil, lemon oil, orange oil, thistle oil, tomato seed oil, almond oil, perilla oil, canola oil, pistachio oil, hazelnut oil, avocado oil, and the like, and mixtures or fractions thereof.

In one embodiment of the present disclosure, the composition may include at least two edible oils. For example, one embodiment contains a mixture of only coconut oil and canola oil. However, in another embodiment of the present disclosure, the composition may include three edible oils, such as olive oil, coconut oil, and canola oil. In other embodiments of the present disclosure, different combinations of edible oils may exist.

Figure 3:
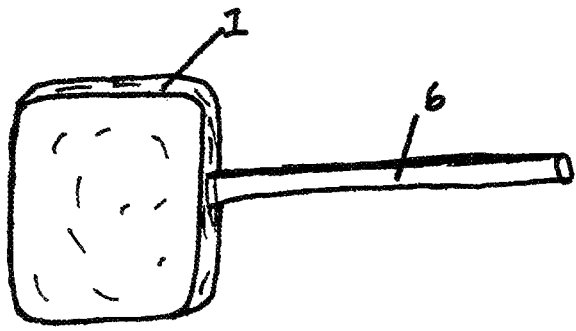
FIG. 3 is a perspective view of an exemplary embodiment of the frozen form according to the present disclosure attached to a stick that the patient may use to hold and/or administer the frozen product.
Figure 4:
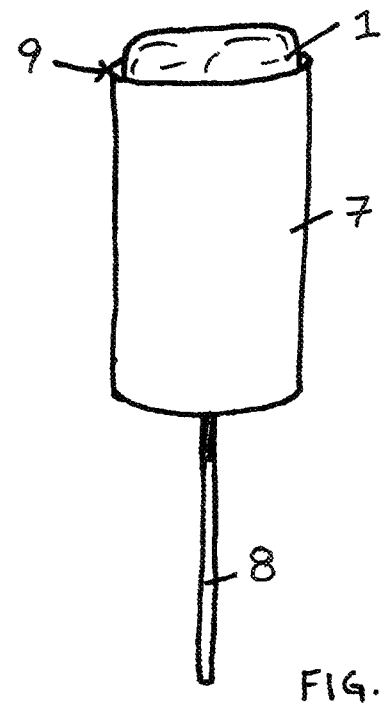
FIG. 4 is a perspective view of an exemplary embodiment of at least a partially frozen form according to the present disclosure in a tube packaging, wherein a stick may be pushed upwardly and/or outwardly so that the product becomes at least partially accessible at a top of the tube for consumption and/or administration.

It may also be desirable to produce an edible oil composition or mixture in at least a partially or completely frozen form because it may be the case that the most effective application is when the composition is in a frozen state. For example, as shown in FIG. 3, the edible oil composition, generally designated 1, may be adhered to or at least partially frozen around or on an end of a stick 6. Similarly, as shown in FIG. 4, the at least partially frozen composition 1 may be at least partially contained within a tube 7 and movable by a rod or piston 8, whereby the piston may expose at least a portion of the composition 1 for consumption at one end 9 of the tube 7. In such an embodiment, the composition 1 may include only one edible oil. Upon freezing or refrigeration of the edible oil composition 1, the volume, depth and/or width of the composition 1 will be greater than that of pure liquid oil composition. This may allow the patient to more easily move the item or at least a portion of the composition 1 around in his or her mouth or at least partially chew it before swallowing, or to simply allow the item to dissolve into the mouth while effectively moisturizing at least some oral tissues, and at least portions of the lips and/or throat.

In some embodiments, at least one edible oil may be extra virgin, virgin, unrefined, or refined coconut oil or olive oil. Olive oil and coconut oil have widely different melting temperatures (approximately 21 degrees Fahrenheit and 76 degrees Fahrenheit, respectively) and both have trending health benefits in the marketplace. These contrasting temperatures allow for mixtures of the oils to have properties that will help with the mouth feel of the composition of the present disclosure by providing a frozen embodiment that is not too hard to chew and swallow.

At least some embodiments of the present disclosure utilize high fat concentrations, which make them unique to the frozen or cold food category. For example, ice cream is typically packaged in a barrier container and may contain a minimum of 10% fat and around a maximum of 16% fat. In the prior art, significant attention has been directed toward reducing the fat and cholesterol contents within these items. The composition of the present invention, however, can include a high percentage of fat content, such as approximately 60-100% fat content. The high fat concentration in at least some of the embodiments of the composition of the present disclosure exceeds the maximum amount found in ice cream products. Consuming fats at this level are not known in the prior art to be desirable for direct consumption.

In the frozen or cold food category, oils are also used in ice cream coatings, formerly known as compound coatings. Compound coatings use a percentage of vegetable oils ranging from 28% to 70% fat, which is greater than the percentage of fat found in ice cream. It is known that above 65% fat content is considered extremely high for a compound coating. Compound coatings, however, are not consumed alone. The compound coatings act as the barrier to protect the interior of ice cream and other soft serve frozen edible novelty products, to maintain their (e.g., ice cream) character as a cohesive and solid mass when exposed to a temperature above ice cream or frozen edible novelty product's melting point, to resist drippage as the ice cream or other soft serve frozen edible novelty product melts, and to be able to be conveniently served and consumed at a higher temperature than those without the compound coatings, and at times to allow the consumer to grasp the item with their hands.

Therefore, since compound coatings are exposed directly to air, and ambient temperature often above ice cream or other soft serve frozen edible novelty product's melting point and to the consumer's hands, they need to be delivered at a melting point of about 75 degrees Fahrenheit to 105 degrees Fahrenheit. This melting temperature range may create a harder texture, thereby creating less overall lubrication in the consumer or patient's mouth. However, at least some of the frozen or cold embodiments of the present disclosure can have a melting point that is substantially lower than 75 degrees Fahrenheit. Because the composition of the present disclosure is produced with different packaging then the way in which compound coatings are typically formed, this allows for a significant decrease in the melting temperature below 75 degrees Fahrenheit and an increase in the percentage of the edible oils (e.g., in excess of 60%), thus providing a more intense and/or desirable moisturizing sensation in the mouth without the undesirable effects of a messy, soft product.

Packaging can be extremely important in how consumers use a product. In the dietary supplement industry, products such as coconut oil, fish oil, and medium chain triglycerides (MCT) oil, are used directly for a variety of different health benefits. Typically the consumer can buy these items in a few different packaging forms. The oils can be packaged in a glass container, in capsule form, or in a plastic container rather than glass. All of these forms are sold and known to be used at room temperature.

Oils packaged directly in glass containers and also in capsules are not conducive for freezing, because the glass would break and the capsule adds no extra benefit from being frozen. Plastic containers are used for highly saturated fats such as coconut oil, which could be placed in the freezer; however, due to the increased melting point of highly saturated fats, the freezer will create disappointment for the consumer as it will be difficult to then scoop or use the product after being frozen. Other oils that are low in saturated fats and thus more freezer compatible are also packaged in plastic containers. However, these containers and bottles are only conducive for pouring and not scooping, which makes sense because unsaturated fats have lower melting points and are usually liquid at room temperature. Therefore, freezing the item would make it extremely hard for the consumer to use the oil as the top of the bottle or container has a very small opening. Thus, packaging in the dietary supplement industry does not make it conducive or beneficial for freezing. The packaging of at least some embodiments of the present disclosure contains the composition or edible oils in a barrier, which allows for such a high concentration of oils with a lower melting temperature than what is typically found in the comparable compound coating range.

At least one difference between the frozen or cold embodiment of the present disclosure and other frozen products in the marketplace is the functionality of the present disclosure (e.g., the targeted prolonged moisturizing sensation). Most conventional frozen product manufacturers are attempting to decrease calories and fat. While in contrast, it is important for the composition of the present disclosure to deliver calories in the form of moisturizing edible oils because specific patient groups are struggling from malnutrition due to the lack of ability to swallow and consume foods.

In another embodiment, the composition of the present disclosure can be refrigerated upon administration. In yet another embodiment, the oil composition of the present disclosure can remain at a relatively warm temperature upon administration. In at least one embodiment, the desired functionality of the oil composition of the present disclosure can be effective at any desirable temperature for the patient's mouth, provided that the temperature of the composition does not cause more pain in the mouth due to a particular patient's condition. In some embodiments, the composition is enclosed in a package.

Figures 5, 6:
FIG. 5 is a perspective view of another exemplary form of cup packaging containing an exemplary embodiment of a frozen form according to the present disclosure, wherein the frozen form is concealed beneath a removable cover or top.
FIG. 6 is an exemplary nutrition label for one or more of the packaging containing the exemplary forms described herein.

For example, as shown in FIG. 5, a removable lid 10 may be attached to a cup or bowl 2 containing the edible composition (not shown). A portion of the lid 10, such as a flap 11, may extend significantly beyond the outer perimeter of the cup 2 than the remaining portions of the lid 10, so as to aid in separation or removal or the lid 10 from the cup 2. The cup 2 may include a wide top or opening to enable spoon insertion to enable to patient or a healthcare working to scoop out the composition within the cup 2.

In other embodiments of the present disclosure, packaging may be essential for success in the deliverance of the edible oil composition to the patients. The packaging may allow the consumer to grasp the edible oils more conveniently at ambient temperatures without the drippage and loss of cohesiveness. Drippage or loss of cohesiveness can result in soiled hands, clothing, and the like if care is not taken when these edible oils are eaten from the packaging held by their hands. It is also possible to provide a packaging design to have the ability to deliver the item to a patient who cannot actually grasp it on his own. For example, the composition may be packaged in different forms and materials.

In some embodiments of the present disclosure, the composition may be packaged in frozen, refrigerated, or room temperature form. In some embodiments of the present disclosure, the composition may be packaged in a tube 7 (see FIG. 4), provided in a cup or bowl 2 (see FIG. 1) and accessible by a spoon, for example. In some embodiments of the present disclosure, the composition may be packaged in a bag, a blister pack, surrounded by a film, or in a pouch application. Suitable examples of the materials of the packaging include, but are not limited to, paper or plastic forms.

In another embodiment, the composition is sealed in the package. The packaging may be a one, two, three, or four sided, sealed and flexible application.

In a further embodiment, the packaging may be portion controlled, yet still provide patients with a sufficient amount of calories in smaller bites. Suitable patients for the composition of the present disclosure are those who are struggling to eat and do not want to consume large amounts of a supplement or food, especially if they are having difficulty swallowing. Therefore, the composition can be in portioned packaging to limit the amount of movement in the mouth and swallowing required due to the decreased amount of portioned product that they are ingesting. Specific oils, like coconut oil and olive oil, may be preferred in such an embodiment. Edible oils may be preferred due to their desirable melting points, interaction with other oils, health benefits, and allergen impact, for example.

Patients that want to consume a product with varying degrees of thickness for swallowing purposes can use a tube 7 (see FIG. 4), a cup or bowl 2 (see FIG. 1), film, bag, a one, two, three, or four sided sealed package, and/or pouch containing various degrees of formula thickness. Specific thickeners may be added to the formulation containing saturated and unsaturated fats. Such an embodiment may be consumed at room temperature, refrigeration temperature, or at a frozen temperature. This specific embodiment may be designed for patients who are looking for calories, lubrication, and an aid in swallowing (e.g., Dysphagia patients). Such a composition will still be lubricating, but may be a bit thicker and viscous than certain embodiments described herein.

In one embodiment, a frozen composition including at least one edible oil is packaged into a one, two, three, or four sided sealed plastic bag. In another embodiment, the package can be produced and shipped at room temperature and then frozen upon arrival at the final destination.

In another embodiment, as described above, the packaging of the edible product or composition 1 may allow the product to be consumed by a patient holding a stick 6 or piston 8 (see FIGS. 3 and 4) attached to the at least frozen edible oil composition 1. In other embodiments, the composition can be found without a stick and can be produced in both bite size (e.g., individually wrapped) and larger shapes (e.g., the size of an ice cream bar). In a further embodiment, the stick, bite size and bar form may be packaged in a wrapped seal, bag, or cup. In a further embodiment, as described above and shown in FIG. 4, the packaging may include a cylindrical tube 7 and stick mechanism or piston 8 for the patient to consume the composition 1 by pushing on at least a portion of the piston 8, thereby causing the composition 1 to at least partially come out of the tube 7 at one end 9 thereof. Ultimately, the composition 1 of such an embodiment may be less moisturizing to a patient's mouth, because the melting temperature of the composition would need to be higher in order to provide a thickness that could support the structure of the composition. Similar to the compound coatings addressed above, the melting temperature would need to be higher and, thus, such an embodiment may provide overall less lubrication. For example, coconut oil or other high melting temperature oils may be included in the composition to texturize and thicken the product. In contrast to an edible compound coating, this product or composition may have more volume and mouth-feel benefits. Thus, the ability to grasp the product without a drippage or other mess would increase significantly and the patient would be more satisfied.

An alternative embodiment may include the composition in a polymeric, elongated pouch, where one end of the pouch may be opened (e.g., cut with scissors) to expose and thereby consume at least some of the composition. At least some of the composition may be removed from the pouch by pushing or compressing (or pull) a portion of the pouch away from or toward the opening.

Figure 2:
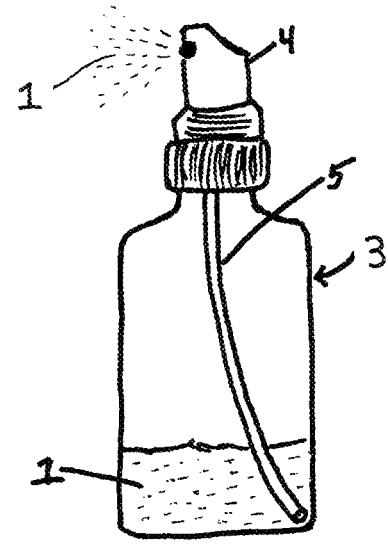
FIG. 2 is a perspective view of an exemplary form of spray-bottle packaging, which includes a storage area containing an exemplary embodiment of a liquid form according to the present disclosure.

Referring to FIG. 2, patients that want convenience and fewer, yet significant, calories from a composition for dry mouth relief may use a spray bottle packaging, generally designated 3, which allows for delivery or administration of the composition 1 in the form of liquid in a mist or spray. In this packaging application, the blend of the composition 1 may contain one or more edible oils, excluding highly saturated fats, such as coconut oil due to the thickness of the oil and the potential for clogs due to such fats in the sprayer 4. For example, one embodiment may include a composition with a mixture of olive oil and canola oil. Oils that are in the liquid state at room temperature may be used in this packaging. The composition 1 may be cooled, but it is not recommended to be placed in the freezer as this may thicken/freeze the oils and potentially cause the sprayer 4 or inner tube or straw 5 to clog. Water may also be added to the composition for impact on texture and efficacy of spray. This alternative of spray bottle packaging may be recommended for those who want lubrication, but want to control caloric intake (e.g., Sjögren's syndrome patients).

In one embodiment, the composition may be formed of 0.01-49% olive oil, 10-85% coconut oil, and 15-90% canola oil. The above percentages create a desirable mouth feel, taste, and sensation in the mouth and throat of a patient. The composition may have a melting temperature of oil formation in the range of 0-75 degrees Fahrenheit. In another embodiment of the present disclosure, such as with use of the spray bottle 3 (see FIG. 2), the composition may include highly unsaturated fats and comprise 25-100%, canola oil, 25-100% olive oil, and 0.01-75% water ($H_2O$). Stated differently, the composition may include 25-100% oil and 0.01-75% water. The melting temperature range for the composition of the spray bottle application may be −15-75 degrees Fahrenheit. More specifically, the composition may include a unique blend of plant oils (e.g., canola oil, coconut oil, olive oil), purified water, cane sugar, natural lemon and tropical flavors.

As understood by those skilled in the art, the composition of the present disclosure may provide essential amounts of calories to the patients. Therefore, the present disclosure serves both functional and health related benefits by delivering calories and providing a soothing benefit to the mouth, lips, and throat. The formulas and/or compositions described above can also be added into other foods and supplements for lubrication and nutritional benefits. FIG. 6 shows an exemplary nutrition label, generally designated 12, for the composition according to at least one embodiment of the present disclosure. The edible composition may provide approximately 235 calories per serving, which is considered to be in the range defining an appreciable amount of calories for a patient.

In some embodiments, supplementary ingredients may be added to the composition, such as for added health and functionality purposes. In one embodiment, the composition may include at least one or two or more vitamins. The vitamin may be selected from the group consisting of Vitamin A, Vitamin B, Vitamin C, Vitamin D, Vitamin E, Vitamin K, and any combinations thereof. In the same or another embodiment, the composition may include at least one mineral (e.g., table salt) and/or at least one mineral element in a suitable form (e.g., salt, compound, chelated, etc.). Examples of minerals include, but are not limited to, calcium, phosphorus, potassium, sodium, chloride, magnesium, sulfur, iron, iodine, zinc, chromium, selenium, fluoride, molybdenum, copper, manganese, and any combinations thereof. In another embodiment, the composition may include alternative or additional nutritional elements, such as protein, fiber, and amino acids.

In addition to delivering nutrition and calories, the functionality of the oral component of the present disclosure is important. The composition may include at least one desirable melting temperature point, which will provide a moisturizing sensation in the mouth, lips, and in the throat. In some embodiments, the composition will also coat at least a portion of the mouth and allow for consumption of other compositions. In other embodiments, ingredients may be used to complement the oral component of the invention, such as xylitol, menthol, eucalyptus oil, lemon, mint, peppermint, spearmint, essential oils, aloe vera, tea tree, malic acid, citric acid, and tartaric acid. In another embodiment, demulcents like pectin, honey, glycerin, and syrup may be used to help with throat irritation. Additionally, synthetic demulcents, such as methyl cellulose, propylene glycol, and glycerin may be used for some audiences.

It may also be beneficial to add other ingredients to stabilize the product or composition, and also add specific functionality. In some embodiments, an aqueous base may be added with edible oils for functionality, texture, and health purposes. An aqueous base may be helpful to decrease the amount of saturated fats in compositions using certain edible oils. In other embodiments, the other ingredients may include sugar, lecithin, gums, emulsifiers, thickeners, flavoring agents, coloring agents, and the like. In some embodiments, cream, milk, fruit and vegetables in the form of juice or purees, or water may be blended with the edible oil composition, which may contribute to or enhance the satisfying mouth feel of the composition. Flavors of the composition may be directly linked to creaminess, which may both enhance desirability.

An aqueous base in the composition will hydrate the consumer's throat as the edible oils are being ingested and swallowed. An aqueous base will increase the movement of the formulation and thus alleviate coughing due to the slow movements of the oils. It may be important to use an efficient amount of water to compensate for the texture, flavor, melting temperature, lubrication to the mouth and throat, as well as overall desirability. In at least one embodiment of the present disclosure, water may be added at the following percentages: 0.1%-40%. An emulsion may be necessary in such an embodiment. For example, xanthan gum is known to emulsify salad dressings, which contain water and oil. The emulsion at the proper percentage will only bind the product and allow for a more desirable texture during the freezing process.

In some embodiments, the composition may include a therapeutic agent. The terms "therapeutic agent" and "drug" and "agent" are used interchangeably herein to refer to a compound that, when present in a therapeutically effective amount, upon exposure to a site of action, produces a therapeutic effect, and whose site of action is located or whose effect will be exerted on the surface or inside target cells. In some embodiments, the therapeutic agent may be pertinent for the irritation of the mouth or for infection. Such agents may include antibiotic, analgesic, antipyretic, anesthetic, and antifungal agents. In other embodiments, the agent is an antibiotic to kill bacteria around the sore, an antihistamine or local anesthetic to reduce pain and discomfort, an antifungal to reduce fungal growth, a corticosteroid to treat inflammation, or an antacid to enhance coating of the other ingredients inside the mouth. Additionally or alternatively, the composition may include one or more of lecithins, gums, emulsifiers, thickeners, flavoring agents, coloring agents and fruits for stability and desirability in texture, perception and/or flavor.

In use, the composition may be consumed or applied before, during and/or after a meal, or anytime the patient's mouth and/or throat are sore or irritated. Consuming or applying the composition at mealtime will help to coat and soothe the mouth in order to help the patient feel better and allow other foods to be more easily consumed. For the frozen embodiment of the composition 1, a spoon may be used to shave the composition from the cup 2, for example. The shaved composition pieces may be ingested or applied in relatively small amounts to effectuate relief from sore mouth and/or throat. The composition 1 is shelf-stable and does not require refrigeration. However, the patient may desire that the composition 1 is frozen before serving or consumption.

The present disclosure also relates to processes to manufacture the composition described in detail above. The composition may be prepared or produced in a warm, cool, or frozen environment. In one embodiment, the composition may be filled and sealed through a liquid dispenser. In another embodiment, the edible oil composition may be produced in a frozen production plant. The composition may be produced in a bite size oriented shape, as well as in a longer shape. Both large and small shapes may be produced with a stick for the consumer to grasp upon consumption. In a frozen production plant, the item may be extruded and molded.

The features and advantages of the present disclosure will be readily apparent to those skilled in the art. While numerous changes may be made by those skilled in the art, such changes are within the spirit of the invention. For example, one or more components of any embodiment of the composition may be removed therefrom or added to another embodiment described herein.

We claim:

1. An edible composition comprising:
   1%-40% by weight of water; and
   a mixture of at least two edible oils;
   wherein the edible composition comprises at least 60% oil or fat,
   wherein said edible composition has a melting temperature in the range of from 35 degrees Fahrenheit to 75 degrees Fahrenheit,
   wherein at least one edible oil in the edible composition has a melting temperature above 75 degrees Fahrenheit selected from the group consisting of coconut oil and palm oil and at least one edible oil in the edible composition has a melting temperature below 35 degrees Fahrenheit selected from the group consisting of canola oil, olive oil, sunflower oil and soybean oil;
   an emulsifier;
   sugar; and
   a flavoring agent;
   wherein said edible composition is formulated to alleviate discomfort of oral complications associated with cancer chemotherapy or radiation therapy in a patient.

2. The composition of claim 1, wherein the mixture of at least two edible oils consists of three edible oils.

3. The composition of claim 1, wherein the mixture of at least two edible oils consists of canola oil, coconut oil and olive oil.

4. The composition of claim 1, wherein the mixture of at least two edible oils consists of 0.01-49% olive oil, 10-85% coconut oil and 15-90% canola oil by weight relative to the total weight of the composition.

5. The composition of claim 1 further including
at least one vitamin, wherein the at least one vitamin is selected from the group consisting of Vitamin A, Vitamin B, Vitamin C, Vitamin D, Vitamin E, Vitamin K and any combinations thereof, or
at least one mineral, wherein the at least one mineral is selected from the group consisting of calcium, phosphorous, potassium, sodium, chloride, magnesium, sulfur, iron, iodine, zinc, chromium, selenium, fluoride, molybdenum, copper, manganese and any combinations thereof; or
at least one therapeutic agent.

6. The composition of claim 1, wherein the composition has a melting point substantially lower than 75 degrees Fahrenheit.

7. The composition of claim 1, wherein the composition is at least partially frozen.

8. A combination comprising:
a package selected from the group consisting of a tube, a spray bottle, a cup, a pouch, or a blister pack; and
an edible composition within the package, the edible composition comprising 1%-40% by weight of water and at least two edible oils,
wherein the edible composition comprises at least 60% oil or fat,
wherein said edible composition has a melting temperature in the range of from 35 degrees Fahrenheit to 75 degrees Fahrenheit,
wherein at least one edible oil in the edible composition has a melting temperature above 75 degrees Fahrenheit selected from the group consisting of coconut oil and palm oil and at least one edible oil in the edible composition has a melting temperature below 35 degrees Fahrenheit selected from the group consisting of canola oil, olive oil, sunflower oil and soybean oil;
an emulsifier;
sugar; and
a flavoring agent;
wherein said edible composition is formulated to alleviate discomfort of oral complications associated with cancer chemotherapy or radiation therapy in a patient.

9. The combination of claim 8, wherein the package is a spray bottle, said spray bottle configured to administer the edible composition through a nozzle of the spray bottle.

10. The combination of claim 8, wherein the edible composition is at least partially frozen prior to administering to a patient.

11. The combination of claim 8 wherein the mixture of at least two edible oils consists of 0.01-49% olive oil, 10-85% coconut oil and 15-90% canola oil by weight relative to the total weight of the composition.

12. The combination of claim 8 wherein the composition further includes
at least one vitamin, wherein the at least one vitamin is selected from the group consisting of Vitamin A, Vitamin B, Vitamin C, Vitamin D, Vitamin E, Vitamin K and any combinations thereof, or
at least one mineral, wherein the at least one mineral is selected from the group consisting of calcium, phosphorous, potassium, sodium, chloride, magnesium, sulfur, iron, iodine, zinc, chromium, selenium, fluoride, molybdenum, copper, manganese and any combinations thereof; or
at least one therapeutic agent.

13. The combination of claim 8, wherein the composition has a melting point substantially lower than 75 degrees Fahrenheit.

* * * * *